United States Patent
Cavagna et al.

(10) Patent No.: US 7,128,895 B2
(45) Date of Patent: Oct. 31, 2006

(54) USE OF BILE ACID DERIVATIVES CONJUGATED WITH METAL ION CHELATED COMPLEXES FOR THE DIAGNOSTIC ASSESSMENT OF MICROVASCULAR PERMEABILITY

(75) Inventors: Friedrich Cavagna, Milan (IT); Timothy P. L. Roberts, San Francisco, CA (US)

(73) Assignees: Bracco Imaging S.p.A., Milan (IT); The Regents of the University of California, Oakland, CA (US)

( * ) Notice: Subject to any disclaimer, the term of this patent is extended or adjusted under 35 U.S.C. 154(b) by 276 days.

(21) Appl. No.: 10/257,533

(22) PCT Filed: Apr. 17, 2001

(86) PCT No.: PCT/EP01/04324

§ 371 (c)(1),
(2), (4) Date: Oct. 24, 2002

(87) PCT Pub. No.: WO01/82974

PCT Pub. Date: Nov. 8, 2001

(65) Prior Publication Data

US 2003/0103904 A1     Jun. 5, 2003

(30) Foreign Application Priority Data

Apr. 21, 2000  (IT) .................. MI2000A000899

(51) Int. Cl.
*A61B 5/055*     (2006.01)
(52) U.S. Cl. .................. 424/9.36; 424/9.1; 424/9.2; 424/9.3; 424/1.45; 424/1.65
(58) Field of Classification Search .............. 424/1.11, 424/1.37, 1.45, 1.65, 9.1, 9.3, 9.32, 9.322, 424/9.36, 9.361, 9.364, 9.365; 534/7, 10–16
See application file for complete search history.

(56) References Cited

U.S. PATENT DOCUMENTS

| 5,649,537 | A | 7/1997 | Anelli et al. |
| 6,461,588 | B1 | 10/2002 | Anelli et al. |
| 6,803,030 | B1 | 10/2004 | De Haen et al. |
| 2003/0103904 | A1* | 6/2003 | Cavagna et al. ......... 424/9.365 |

FOREIGN PATENT DOCUMENTS

| WO | 90/03801 A | 4/1990 |
| WO | 95/19186 A | 7/1995 |
| WO | WO 95/32741 | * 12/1995 |
| WO | 00/38738 A | 7/2000 |
| WO | WO 00/38738 | 7/2000 |
| WO | WO 01/64708 A1 | 9/2001 |

OTHER PUBLICATIONS

Curtis et al (Oct. 1995), vol. 79, No. 4, pp. 1351-1360.*
Reber (1985) Scandinavian Journal of Gastroenterology, Supplement, vol. 20, Suppl. 112, pp. 96-100.*
Betebenner et al; "Hepatobiliary Delivery of Polyaminopolycarboxylate Chelates: Synthesis and Characterization of a Cholic Acid Conjugate of EDTA and Biodistribution and Imaging Studies With its Indium-111 Chelae"; Bioconjugate Chemistry, American Chemical Society, Washington, US, vol. 2, No. 2, 1991, pp. 117-123, XP002137988.
Maeda et al; "Tumor Vascular Permeability and the EPR Effect in Macromolecular Therapeutics: A Review", Journal of Controlled Release, Elsevier Science Publishers B.V., Amsterdam, NL, vol. 65, No. 1-2, Mar. 2000, pp. 271-284, XP004190328.

* cited by examiner

*Primary Examiner*—Dameron L. Jones
(74) *Attorney, Agent, or Firm*—Nixon & Vanderhye P.C.

(57) ABSTRACT

The use of contrast agents of molecular weight lower than 5000 Dalton and including at least one residue of a biliary acid for the preparation of diagnostic contrast compositions for the microvascular permeability assessment is disclosed.

17 Claims, No Drawings

USE OF BILE ACID DERIVATIVES CONJUGATED WITH METAL ION CHELATED COMPLEXES FOR THE DIAGNOSTIC ASSESSMENT OF MICROVASCULAR PERMEABILITY

This application is the U.S. national phase of international application PCT/EP01/04324 filed 17 Apr. 2001, which designated the US.

The present invention relates to the use of metal ion chelated complexes for the preparation of pharmaceutical formulations for the diagnostic assessment of microvascularized systems.

The structure of solid tumors is generally unsettled, fundamentally chaotic, in contrast to the elegant and ordered anatomical design of normal tissues and organs. Solid tumor and, in particular, malignant tumor microcirculation differs profoundly from that of a normal organ. The variation of the capillary density is mainly due to the vascular endothelial grown factor (VEGF), also known as vascular permeability factor (VPF), which is elaborated by the tumor cells or tumor-associated inflammatory cells. This factor activates the host endothelial cells to produce new microvessels starting from preexisting blood vessels, according to a process known as angiogenesis. Besides the promotion of angiogenesis process, the VEGF/VPF factor has shown to further affect the maturation of new small vessels, wherein said phenomenon is known as vasculogenesis.

Main modifications led by the presence of a solid tumor in particular relate to the flow characteristics and/or to the blood volume of the microvasculature, wherein the blood flow is both spatially and temporally more heterogeneous than the efficient, uniform perfusion of normal organs and tissues. In addition to these abnormalities, microvascular permeability in tumors is often markedly modified. The VEGF/VPF factor, in fact, can considerably increase the microvessels permeability to the macromolecular components of the plasma and it is also responsible for the modification of the extravascular-extracellular volume fraction which in a tumor is abnormally higher than the vascular and intracellular fraction.

Moreover, when a tumor is present, generally, the capillary endothelium is also injured.

The diagnostic imaging based on the Nuclear Magnetic Resonance principles, known as Magnetic Resonance Imaging (M.R.I.), is a well known method of imaging which constitutes a powerful aid for everyday clinical investigations. In particular, when the diagnostic imaging is performed after the administration of some suitable contrast agents, this diagnostic method allows both the diagnostic evaluation of the functionality as well as the morphologic assessment of the examined organ and tissues.

A further opportunity offered by the Magnetic Resonance Imaging is the dynamic imaging, a diagnostic technology which allows the visualization of signal intensity variations over the time in an organ or tissue of interest. In particular, when applied in association with the administration of contrast agents this technology provides useful information on the physiological properties and conditions of the examined organs and/or tissues.

Microvascular hyperpermeability to macromolecular solutes is a well-known characteristic of tumor microvessels. (Am J Pathol 146:1029–1039, 1995; Microvasc Res 1986, 31, 288–305).

Macromolecular contrast media, which in healthy tissues remain largely confined into the vascular space, diffuse through the altered or diseased endothelium and/or the hyperpermeable vascular endothelium of malignant tumors into the interstitial spaces, progressively increasing tissue enhancement, that is to say the intensity of the signal registered in said tissue. The signal intensity registered in a tissue refers to the brightness of the imaged tissue: the brighter is the tissue, the higher is the signal intensity in said tissue.

Magnetic Resonance Imaging of tumors, in particular when enhanced by the use of macromolecular contrast agents, is based on and takes advantage of said differences existing among microvessels permeability.

In particular, dynamic Magnetic Resonance Imaging in association with the administration of contrast agents, also known as Dynamic Contrast Enhanced MR Imaging, (DCE MRI), is a promising method which allows the non-invasive, in vivo tumor monitoring and the generation of quantitative measures which closely correlate with either the tumor angiogenic activity or the histopathologic grading of tumor mass.

The dynamic contrast enhanced MR Imaging can also advantageously detect and measure the malignant tumor response to antiangiogenesis (e.g. anti-VEGF antibody) drugs and can further constitute a valid support to perfect the efficacy of a chemotherapeutic agent, allowing the evaluation of its most effective dose and of the powerful irradiation time.

At the present time, the only contrast agents suitable for these purposes are the macromolecular agents.

In an injured tissue and in tumors where the capillary endothelium exhibits higher permeability than normal tissue does, the contrast agent passively diffuses through the endothelial barrier into interstitial space, where it gradually accumulates, allowing a progressive increase in tissue enhancement. The rate of enhancement increase relates, by means of appropriate kinetic models, to microvessel permeability to the contrast agent in said particular tissue. Quantitative ratio between signal enhancement in a particular tissue and the enhancement registered at the same time point in a region totally constituted by blood (the inferior vena cava, for example) is a parameter which can be correlated with the fractional plasma volume (fPV) of said tissue.

Tumor assessment by DCE MRI is fundamentally based on the quantitative evaluation of said MR imaging-derived characteristics, that is to say the vascular degree or fractional plasma volume (fPV) of the tissue and the endothelial transfer coefficient or macromolecular permeability ($K^{PS}$) which, in a malignant tumor, are abnormal and significantly higher that those obtained for a soft, non neoplastic tissue.

In experimental tests, dynamic MRI imaging of microvascularized systems is normally performed following the administration of macromolecular contrast agents. Particularly preferred are contrast agents with molecular weights higher than 20.000 Dalton.

So far, albumin-$(Gd-DTPA)_{30}$ (m.w. ≅92 kD) and the polylysine-Gd-DTPA. are the most frequently used.

Recently, similar studies have also been performed with Gd-DTPA-24-cascade polymer, a macromolecular contrast agent comprising 24 Gd ions, whose molecular weight is 30.000 Dalton.

In particular U.S. Pat. No. 6,009,342 relates to an imaging method of determining the pathologic grade of a tumor comprising the administration of a macromolecular contrast medium to the animal under examination. The preferred macromolecular agent for the claimed method is the albumin-$(Gd-DTPA)_{30}$.

However, no one of these macromolecular contrast agents will be likely to enter clinical trials because of incomplete elimination and potential for toxicity or immunogenic response they have shown (JMRI 1997; 7:331–338).

The literature also describe experimental DCE MRI derived quantitation of the microvessels permeability, and histologic tumor grading test performed following the administration of low molecular weight gadolinium chelates, particularly Gd-DTPA (m.w. 500 Dalton), which, on the contrary, is an agent already approved and marketed as Magnevist®. The teaching emerging from the results of these studies is that low molecular weight contrast agents are not able to differentiate a healthy tissue from a pathologic tissue including injured or hyperpermeable microvessels. Low molecular weight contrast agents, in fact, readily diffuse across endothelial walls of both normal vessels and neoplastic capillaries and in both cases rapidly equilibrate between the intravascular and interstitial compartments of the organ.

Permeability measures estimated by low molecular weight contrast agents enhancement data neither show any significant correlation with the presence of a malignant tumor nor correlate, in any diagnostically useful extent, with the histopathologic grading of the tumor itself. (Magn Reson Med 2000, 55(6): 915–924; AJR: 171, 1998, 941–949; JMRI 1997, 7: 82–90).

Unspecific results were also obtained using FITC-dextran (m.w. 3 kDa).

Tumor represents one of the most important and ravaging human diseases; the improvement of both specificity and sensitivity of contrast agents used to manage patients affected by this pathology is therefore a medical need and a target for scientific research.

Now, contrary to the teaching derived from the above examined state of the art, we have surprisingly found that a particular class of contrast agents of quite low molecular weight can advantageously be used for the preparation of pharmaceutical formulations for the dynamic assessment of microvascularized systems.

The present invention relates to the new use of a particular selection of compounds having a molecular weight lower than 5000 Dalton, preferably between 4500 to 500 and more preferably between 3000 to 500 Dalton which include in their structure at least a biliary acid residue, for the preparation of contrastographic formulations for the diagnostic visualization of microvascularized systems, in particular wherein the relative tissue plasma volume is determined and/or the microvessels permeability as well as integrity are measured.

In particular, the invention relates to the new use of a class of compounds including in their molecular structure at least one, and preferably one, biliary acid residue and at least one, but not more than two, chelated complex units of bi or trivalent paramagnetic metal ions, as well as the salts thereof with physiologically compatible organic bases selected from primary, secondary, tertiary amines or basic amino acids, or with inorganic bases whose cations are selected from sodium, potassium, magnesium, calcium or mixtures thereof for the MRI dynamic imaging of the integrity as well as of the microvascular permeability of a microvascularized system and for the determination of the vascular degree of an animal or human organ and/or tissue.

The compounds of the invention and the preparation thereof have already been disclosed in detail by the Applicant in U.S. Pat. No. 5,649,537, U.S. Pat. No. 6,461,588 and U.S. Pat. No. 6,803,030, that are hereby incorporated by reference.

In the compounds of the invention the biliary acid residue is preferably selected from biliary acids obtained by bio-conversion or synthetic modification of the cholesterol. Particularly preferred is the biliary acid residue deriving from cholic, deoxycholic, chenodeoxycholic, ursodeoxycholic, lithocholic acids, as such or as a derivatives thereof, including either those in which the hydroxy groups are functionalized or the taurine and glycine conjugated to the carboxy group at the 24-position of the cholane skeleton.

Preferably, the chelating units of the invention are either linear or cyclic polyaminopolycarboxylic acid residues, the paramagnetic bi or trivalent metal ions chelated to said chelating units, are preferably selected from the group consisting of gadolinium (III), iron (III), iron (II), manganese (II), manganese (III), chromium (III), copper (II), dysprosium (III), ytterbium (III), terbium (III), europium (III) and most preferably are gadolinium (III) and manganese (II).

Preferred cations of inorganic bases suitable for salifying the chelated complexes of the invention particularly comprise the ions of alkali or alkaline-earth metals such as potassium, sodium, calcium, magnesium, and mixtures thereof.

Preferred cations of organic bases suitable for this purpose comprise, inter alia, those obtained by protonation of primary, secondary and tertiary amines such as ethanolamine, diethanolamine, morpholine, glucamine, N-methylglucamine, N,N-dimethylglucamine.

Anions of inorganic acids optionally suitable for the same purpose preferably include the ions of halo acids, i.e. chlorides, bromides, iodides or different ions such as, for example, the sulphate ion.

Anions of organic acids optionally suitable for salifying the chelated complexes of the invention particularly include those of the acids normally used in pharmaceutics for salifying basic substances such as, for example, acetate, succinate, fumarate, citrate and maleate.

Preferred cations and anions of amino acids comprise, for example, those of taurine, glycine, lysine, arginine or ornithine or of the aspartic and glutamic acid.

Preferred is the use according to the invention of a contrast agent characterized in that said agent include in their structure only one chelated complex unit wherein the chelating unit is a linear polyaminopolycarboxylic acid residue, the biliary acid residue of the agent derives from a cholic or a deoxycholic acid and the metal ion chelated to the chelating unit is the gadolinium (III) or the manganese (II) paramagnetic ion.

More preferred is the use according to the invention of compounds whose chelating agent is selected from the following group:

[3β(S),5β]-3-[[4-[bis[2-[bis(carboxymethyl)amino]ethyl]amino]-4-carboxy-1-oxobutyl](carboxymethyl)amino]cholan-24-oic acid;

[3β(S),5β]-3-[[4-[bis[2-[bis(carboxymethyl)amino]ethyl]amino]-4-carboxy-1-oxobutyl]amino]cholan-24-oic acid;

[3β(S),5β]-3-[[4-[bis[2-[bis(carboxymethyl)amino]ethyl]amino]-4-carboxy-1-oxobutyl]amino]-12-oxocholan-24-oic acid;

[3β(S),5β,7α]-3-[[4-[bis[2-[bis(carboxymethyl)amino]ethyl]amino]-4-carboxy-1-oxobutyl]amino]-7-hydroxycholan-24-oic acid;

2-[[[3β(S),5β]-3-[[4-[bis[2-[bis(carboxymethyl)amino]ethyl]amino]-4-carboxy-1-oxobutyl]amino]-24-oxocholan-24-il]-amino]ethanesulfonic acid;

[3β(S),5β,12α]-3-[[4-[bis[2-[bis(carboxymethyl)amino]ethyl]amino]-4-carboxy-1-oxobutyl]amino]-12-hydroxycholan-24-oic acid;

[3α(S),5β]-3-[2-[[5-[bis[2-[bis(carboxymethyl)amino]ethyl]amino]-5-carboxypentyl]amino]-2-oxoethoxy]cholan-24-oic acid;

[3β(S),5β,7α, 12α]-3-[[4-[bis[2-[bis(carboxymethyl)amino]ethyl]amino]-4-carboxy-1-oxobutyl]amino]-7,12-dihydroxycholan-24-oic acid;

[3β(S),5β,7α, 12α]-3-[[4-[[5-bis[2-[bis(carboxymethyl)amino]ethyl]-amino]-5-carboxypentyl]amino]-1,4-dioxobutyl]amino]-7,12-dihydroxycholan-24-oic acid;

(3β,5β,7α,12α)-3-[[[bis[2-[bis(carboxymethyl)amino]ethyl]amino]-acetyl]amino]-7,12-dihydroxycholan-24-oic acid;

(3β,5β)-3-[[[[[bis[2-[bis(carboxymethyl)amino]ethyl]amino]-acetyl]amino]acetyl]amino]-cholan-24-oic acid;

(3β,5β,7α,12α)-3-[[[[[bis[2-[bis(carboxymethyl)amino]ethyl]amino]-acetyl]amino]-acetyl]amino]-7,12-dihydroxycholan-24-oic acid;

(3β,5β,7α,12α)-3-[[6-[[[bis[2-[bis(carboxymethyl)amino]ethyl]amino]-acetyl]amino]-1-oxohexyl]amino]-7,12-dihydroxycholan-24-oic acid;

(3β,5β,7α,12α))-3-[[N-[N-[2-[[2[-bis(carboxymethyl)amino]ethyl]-(carboxymethyl)amino]ethyl]-N-(carboxymethyl)glycyl]glycyl]amino]-7,12-dihydroxycholan-24-oic acid;

18-[[(3β,5β,7α,12α))-23-carboxy-7,12-hydroxy-24-norcholan-3-yl]amino]-3,6,9-tris(carboxymethyl)-11,18-dioxo-3,6,9,12-tetraazaottadecanoic acid;

10-[3-[[(3β,5β,7α,12α))-23-carboxy-7,12-hydroxy-24-norcholan-3-yl]oxy]-2-hydroxypropyl]-1,4,7,10-tetraazacyclododecane-1,4,7-triacetic acid;

[3β(S),5β,7α,12α]-3-[[4-[[5-[[2-[bis(carboxymethyl)amino]ethyl]-(carboxymethyl)amino]-5-carboxypentyl]amino]-1,4-dioxobutyl]amino]-7,12-dihydroxycholan-24-oic acid;

[3β(S),5β]-3-[2-[[5-[[2-[bis(carboxymethyl)amino]ethyl]-(carboxymethyl)amino]-5-carboxypentyl]amino]-2-oxoethoxy]cholan-24-oic acid;

[3β(S),5β,12α]-3-[[4-[[2-[[bis(carboxymethyl)amino]ethyl]-(carboxymethyl)amino]-4-carboxy-1-oxobutyl]amino]-12-hydroxycholan-24-oic acid;

[3β(S),5β]-3-[[4-[[2-[[bis(carboxymethyl)amino]ethyl]-(carboxymethyl)amino]-4-carboxy-1-oxobutyl]amino]-12-oxocholan-24-oic acid;

[3β(S),5β,7α,12α]-3-[[4-[bis[2-[bis(carboxymethyl)amino]ethyl]-amino]-4-carboxy-1-oxobutyl]amino]-7,12-dihydroxycholan-24-oic acid;

[3β(S),5β,7α,12α]-3-[[4-[[5-[bis[2-[bis(carboxymethyl)amino]ethyl]-amino]-5-carboxypentyl]amino]-1,4-dioxobutyl]amino]-7,12-dihydroxycholan-24-oic acid;

[3β(S),5β]-3-[[4-[bis[2-[bis(carboxymethyl)amino]ethyl]amino]-4-carboxy-1-oxobutyl](carboxymethyl)amino]cholan-24-oic acid;

[3β(S),5β]-3-[[4-[bis[2-[bis(carboxymethyl)amino]ethyl]amino]-4-carboxy-1-oxobutyl]amino]cholan-24-oic acid;

[3β(S),5β]-3-[[4-[bis[2-[bis(carboxymethyl)amino]ethyl]amino]-4-carboxy-1-oxobutyl]amino]-12-ossocholan-24-oic acid;

[3β(S),5β,7α]-3-[[4-[bis [2-[bis(carboxymethyl)amino]ethyl]amino]-4-carboxy-1-oxobutyl]amino]-7-hydroxycholan-24-oic acid;

[[[3β(S),5β]-3-[[4-[bis[2-[bis(carboxymethyl)amino]ethyl]amino]-4-carboxy-1-oxobutyl]amino]-24-oxocholan-24-yl]amino]ethanesulfonic acid;

[3β(S),5β,7α]-3-[[4-[bis[2-[bis(carboxymethyl)amino]ethyl]amino]-4-carboxy-1-oxobutyl]amino]-12-hydroxycholan-24-oic acid;

[3α(S),5β]-3-[2-[[5-[bis[2-[bis(carboxymethyl)amino]ethyl]amino]-5-carboxypentyl]amino]-2-oxoethoxy]cholan-24-oic acid;

[3α[3(S),4(S)],5β,12α]-3-[[[trans-3,4-bis[[[5-[bis[2-[bis(carboxymethyl)amino]ethyl]amino]-5-carboxypentyl]amino]carbonyl]-1-pyrrolidinyl]carbonyl]oxy]-12-hydroxycholan-24-oic acid;

[3α[3(S),4(S)],5β,12α]-3-[[[trans-3,4-bis[[[2-[bis[2-[bis(carboxymethyl)amino]ethyl]amino]-2-carboxyethyl]amino]carbonyl]-1-pyrrolidinyl]carbonyl]oxy]-12-hydroxycholan-24-oic acid;

(3α,5β,12α)-3-[[[trans-3,4-bis[[[2-[[[4,7,10-tris(carboxymethyl)-1,4,7,10-tetraazacyclododec-1-yl]acetyl]amino]ethyl]amino]carbonyl]-1-pyrrolidinyl]carbonyl]oxy]-12-hydroxycholan-24-oic acid

[3α[3(S),4(S)],5β,12α]-3-[[[trans-3,4-bis[[[5-[[2-[bis(carboxymethyl)amino]ethyl](carboxymethyl)amino]-5-carboxypentyl]amino]-carbonyl]-1-pyrrolidinyl]carbonyl]oxy]-12-hydroxycholan-24-oic acid;

[3α[1(S),2(S)],5β,7α,12α]-3-[[[[cis-1,2-bis[[[5-[bis[2-[bis(carboxymethyl)amino]ethyl]amino]-5-carboxypentyl]amino]carbonyl]-4-cyclopentyl]amino]carbonyl]oxy]-7,12-dihydroxycholan-24-oic acid;

[3α[1(S)],5β,7α,12α]-3-[[[[cis-1-[[[5-[bis[2-[bis(carboxymethyl)-amino]ethyl]amino]-5-carboxypentyl]amino]carbonyl]-2-[[[2-[[[4,7,10-tris(carboxymethyl)-1,4,7,10-tetraazacyclododec-1-yl]acetyl]amino]ethyl]amino]carbonyl]-4-cyclopentyl]amino]carbonyl]oxy]-7,12-dihydroxycholan-24-oic acid;

[3β[3(S),5(S)],5β,7α,12α]-3-[[[3,5-bis[[4-[bis[2-[bis(carboxymethyl)amino]ethyl]amino]-4-carboxy-1-oxobutyl]amino]phenyl]carbonyl]amino]-7,12-dihydroxycholan-24-oic acid.

Particularly preferred is the use according to the invention of the gadolinium complex of the [3(S),5,12]-3-[[4-[bis[2-[bis(carboxymethyl)-amino]ethyl]amino]-4-carboxy-1-oxobutyl]amino]-12-hydroxycholan-24-oic acid chelating ligand as well as of its physiologically compatible salts such as, for example, the trisodium salt.

The trisodium salt of this particular compound is also called from now onwards B22956/1.

The compounds whose use forms the object of the present invention has shown an increased residence time in the vasculature (WO-A-00/38738).

This property is particularly important when a contrast agent is proposed for clinical use in the diagnostic imaging of the vascular system in general and, more particularly, for the dynamic imaging of microvascularized systems, where the microvessels integrity as well as the capillary permeability of the microvascular system are determined.

Surprisingly enough, the compounds according to the invention, in spite of their comparatively low molecular weight, can advantageously be used for the non-invasive in-vivo enhancement of microvessels physiology. In particular, they allow the quantitation of either the microvascular permeability or the fractional plasma volume and consequently can profitably be used for the assessment of angiogenesis and for the microvascular characterization of hypervascularized systems. In this last case, DCE-MRI derived measures obtained by use of the compounds according to the invention, have shown to well correlate with the definition of both physiological conditions such as, for example, embryogenesis, wound healing, corpus luteum formation and growth, and the pathological conditions. Particularly advantageous is the use of the compounds according to the invention for the diagnostic visualization of angiogenesis and for the histopathological grading of the tumor mass based on the quantitative assays of its DCE-MRI derived microvascular permeability characteristics. This use of the agents of the invention allows particularly the non-invasive differentiation of benign from malignant tumors, reducing the need of surgical biopsy, always invasive and traumatic for the patient.

According to the particular use of the agents of the invention, in fact, a simple, substantially linear, favourable correlation between the measured microvascular permeability values expressed as $K^{PS}$ and the histologic characterisation of the tumor mass obtained with the Scarff-Bloom-Richardson grading system (Cancer 64(9), 1989: 1914–1921) was observed. Kinetic models adopted for this purpose, as well as the mathematical processing of MRI derived estimates used to obtain the characterisation of the tumor mass, are similar to those already disclosed in literature, see, for example, MRM 1993; 29:616–622 and AJR: 171, 1998 and cited literature, and are fully described in the experimental section.

Results of an experiment performed in rats either with Albumin-Gd-(DTPA)$_{30}$, the macromolecular agent of the prior art, and with the compounds of the invention, show consistent dynamic enhancement behaviours and lead to the same conclusion: a strong initial enhancement in the tumor tissue followed by a decrease over time, consistent with the enhancement decrease registered in the vena cava, is observed when a benign tumor is present; an enhancement in the tissue which, on the contrary, increases over the time when the blood enhancement decreases is indicative of a malignancy.

On the contrary, permeability experimental estimates obtained after the administration of ProHance®, a low molecular weight contrast agent (m.w.: 558.7 Dalton) also known as Gadoteridol, confirm the absence of any significant correlation between the obtained dynamic signal responses and the presence of a tumor mass as well as with its hystological nature. These indications are consistent with the results obtained when the Gd-DTPA efficacy was tested.

In particular, from the experiment we carried out, as outlined above, in which dynamic MRI data sets from the same tumor-bearing rats were acquired with Albumin-Gd-(DTPA)$_{30}$, ProHance® and B-22956/1 and compared, some facts emerge. The signal tumor enhancement is about ten fold bigger with B-22956/1 than with ProHance®. Additionally, permeability measurements are not significant with ProHance®, because of its quick extraction, while with a macromolecule such as Albumin-Gd-(DTPA)$_{30}$ said measures can potentially be determined with accuracy, but, because the very slow extraction of these agents from the microvasculature, the obtained values are so low that they tend to be buried in the MR signal detection noise. It results quite clear that B-22956/1 represents a good compromise, yielding a quantity which is, perhaps, less simply behaved but surely much more easily observed to be observed than with Albumin-Gd-(DTPA)$_{30}$ and, at the same time, significantly more intense than with ProHance.

Since the angiogenesis process is a key part of tumor progression, a treatment aimed at blocking the angiogenesis will most probably stop or at least delay the tumor development.

The use of the agents according to the invention to further constitute a useful means for monitoring microvascular responses induced by an anti-angiogenic treatment, in particular to predict or non-invasively assess the response of a malignancy to a drug treatment with human anti-VEGF monoclonal antibody. In specific experiments we carried out, microvascular permeability to B-22956/1 was seen to sensibly increase the signal intensity in untreated tumors over a period of nine days. Over the same period such an increase was not observed in animals treated with anti-VEGF antibodies.

Estimates of particular utility are possible when these agents are used to monitor the up-regulated angiogenic process related to the presence of breast malignancies, e.g. human breast carcinoma (MDA-MB-435), although equally favourable outcomes are obtainable when they are used for the diagnostic assessment of many different types of tissues and tumors including, but not limited to, oral cavity tumor, bladder, brain, mammary, cervix, ovaries, pancreas, lung, prostate, soft tissue and central nervous system tumors and carcinomas.

Equally valuable measures and information derive from the monitoring of the malignancy response to chemotherapy or radiation therapy.

The administration of the agents according to the invention further provides reliable definitions of microvascular characteristics in different pathological conditions, i.e. inflammation, myocardial and ischemic states. In fact they allow the assessment of the hyperpermeability of myocardial capillary and the blood extravasation due to the presence of an ischemic tissue.

Nuclear Magnetic Resonance Imaging is the elected diagnostic technique for the new use of the compounds according to the invention.

When the imaging-derived estimates of the fractional plasma volume (fPV) as well of the coefficient of the endothelial permeability ($K^{PS}$) are determined, dynamic imaging is the preferred, even if not limiting, imaging method.

The macromolecular compounds which gave good results when used in experimental tests performed on animals have unfortunately shown some relevant clinical problems due to their incomplete elimination from the body and to possible toxicity and adverse immunogenic reactions.

On the contrary, the results of screening tests performed in rats with the compounds according to the invention, show the complete elimination of the administered agents, normally within a maximum period of 7 days but more generally and preferably within 3 days after the administration. Normally, the administered agents are excreted either with faeces or with urine in an amount depending on either the injected agent or the injected dose. The urinary and faecal elimination results obtained after the administration in rats of B22956/1, the preferred compound for the use according to the invention, are included in the experimental section below. The almost total absence of gadolinium residues in all the examined organs and tissues, that is to say plasma, liver, spleen, femur and kidneys, 7 days after administration of the compound, is a strong indication of the complete elimination of the injected agent. Elimination tests have also been performed with different animal species such as, for example, monkeys and pigs, recovering similar excretion values which confirm the substantially complete elimination of the injected agents.

Moreover, in the interval between B22956/1 administration and sacrifice, no animal showed any clinical sign, even at the highest injected doses.

The agents according to the invention, in fact, have shown to be well tolerated and safe either from a toxicological and an immunogenic point of view.

For the use of the invention the agents are preferably administered parenterally, i.e. intravenously, intraperitoneally, subcutaneously, intradermally or intramuscularly, although, when necessary, different administration routes are not excluded.

Pharmaceutical formulations for parenteral administration are conventionally prepared by dissolving or suspending the contrast agent in a suitable amount of an acceptable carrier, and preferably, an aqueous carrier of suitable pharmacological purity and optionally adding typical galenical excipients, additives and/or salifying agents and can be administered in concentrations ranging between 0.01 to 1.0 M.

These formulations can be conventionally sterilised adopting techniques well known to the expert and can be used as such or lyophilised wherein the lyophilised formulation is normally reconstituted before use by its dissolution in a pharmaceutically acceptable aqueous medium.

Contrast agents according to the invention are administered in variable doses depending on diagnostic need but generally which range between 0.001 to 1.0 mmol/kg of body weight; preferred doses are those ranging from 0.01 to 0.5 mmol/kg of body weight.

MR-Assessment of Microvascular Hyperpermeability in a Rat Breast Tumor Model

Animals

The experimentation is performed on 26 female athymic homozygous rats, purchased from Harlan, Indianapolis, Ind.

Tumor Cell Cultures and Preparation of Implants

Human MDA-MB-435 breast carcinomas (UCSF Cell Culture Facility) is induced in the 26 female six-to-eight-week-old athymic homozygous nude rats.

The human MDA-MB-435 adenocarcinoma cell line is cultured in medium supplemented with 10% foetal calf serum and maintained in a humidified 5% $CO_2$ atmosphere at 37° C. Cells are harvested by trypsinization in ethylenediaminetetraacetic acid/trypsin, washed in PBS and centrifuged at 200 G several times. Approximately $5 \times 10^6$ tumor cells are suspended in a total volume of 0.3 mL (1 part sterile saline: 1 part Matrigel®) and injected with a 25-gauge needle into the mammary fat pads.

Tumor growth is monitored with caliper measurements in two dimensions every second day.

Experimental Protocol

B-22956/1 is administered on day one to a group of 6 rats, ProHance® (10-(2-hydroxypropyl)-1,4,7,10-tetraazacyclododecane-1,4,7-triacetic acid Gd-complex) and Albumin-Gd-(DTPA)$_{30}$ on day two (3 hrs interval between the exams). The animals are then imaged to assess and to understand differences existing among administered contrast agents pharmacokinetic and to compare their MR-derived estimates of microvascular characteristics ($K^{PS}$, fPV).

Results derived with ProHance® and Albumin-Gd-(DTPA)$_{30}$ serve as reference values.

The remaining 20 rats are randomly assigned to the drug or control group.

In particular a dose of 0.2 mL anti-VEGF (or placebo) is administered by intra-peritoneal injection, beginning after the first imaging (=day two); this treatment is applied on the hole three times (=day two, day 5 and, day 8). MR Imaging is performed after drug/placebo-treatment on day 9 and 10.

Immediately after the final MRI session, animals are sacrificed by an intravenous overdose of pentobarbital and subsequent bilateral thoracotomy. The tumor is then resected, fixed in 10% formalin, and used for further possible analyses (for example, CD31 staining for determination of the microvascular density, histologic tumor characterisation).

Imaging Protocol

MR imaging is performed when the implanted MDA-MB-435 breast adenocarcinomas reach a diameter of 10–15 mm. Before MR imaging, animals are anaesthetised with an intraperitoneal injection of pentobarbital (50 mg/kg) and a 23-gauge butterfly needle is inserted in the tail vein for intravenous injection of contrast medium during MR imaging.

Imaging is performed using a CSI-II Omega spectrometer operating at 2.0 T equipped with Acustar S-150 self-shielded gradient coils (±20 G/cm, 15 cm inner diameter). A phantom filled with diluted 0.01 mmol/L gadopentetate dimeglumine will be positioned in the field of view.

The imaging is performed, for example, following this, not exclusive, protocol:

1. Pre-contrast regional $T_1$ determination are made by 3D SPGR (TR=50 ms, TE=1.4 ms, flip angle=10–90°). Matrix 128×128×16, slice thickness 3 mm, FOV 50×50×48. Five different flip angles are used and $T_1$ are determined by curve fitting to the equation:

$$SI=kM_0(1-\exp(-TR/T_1))\sin(\alpha)/(1-\cos(\alpha)\exp(-TR/T_1)),$$

where SI is the signal intensity, $\alpha$ the flip angle, TR the sequence repeat time and $kM_0$ a constant related to magnetisation density.

2. Dynamic "keyhole" (matrix: 128×16×8) 3D-SPGR sequence (TR=30 ms, TE=1.4 ms, flip=90°, Acqu. Time=4 secs) consisting of 3 initial precontrast and 17 dynamic postcontrast images, immediately followed by 20 dynamic 3D-SPGR ("full matrix 128×128×16") post-contrast images with a high spatial resolution and identical parameters (acquisition time=1 min 2 sec).

3. High resolution T1-weighted 3D-SPGR (TR=30 ms, TE=1.4 ms, flip=90°) "late post-contrast" determinations.

MRI Data and Kinetic Analysis

Images are transferred to, processed and analyzed on a Sun Sparc Ultra 1 workstation (Sun Microsystems, Mountain View, Calif.) using the MRVision Software package (The MRVision Co, Menlo Park, Calif.). In each rat and at each time point region of interests (ROI's) are drawn in the phantom, in the inferior vena cava (IVC), and in the tumor periphery. Tumor ROIs are be selected using a semi-automated, signal threshold-based approach in which the most-enhancing pixels on the "late post-contrast" image are identified. This yields an assessment of the most aggressive (most angiogenically active) portion of the tumor.

Dynamic signal responses will be corrected for potential temporal spectrometer variation by normalizing to the signal intensity (SI) of the gadolinium phantom.

Postcontrast R1(=1/T1) values are calculated based on the post-contrast Signal Intensity SI and knowledge of pre-contrast T1 values. Differences between the pre-contrast and postcontrast R1 values at any time are assumed to be proportional to the concentration of the contrast medium, either in the blood or in the tissue of interest according to the equation:

$$SI_{post}/SI_{pre}=(1-\exp(-TR/T_{1post}))/(1-\exp(-TR/T_{1pre})),$$

assuming no change in the signal attenuation factor between pre- and post-contrast states.

Hence:

$$R_{1post}=1/T_{1post}=-(1/TR).\ln\{1-(SI_{post}/SI_{pre}).(1-\exp(-TR/T_{1pre}))\} \Delta R1=R_{1post}-R_{1pre}=1/T_{1post}-1/T_{1pre}$$

The ΔR1 data obtained from blood and tumor are used for kinetic analysis to estimate the coefficient of endothelial permeability, $K^{PS}$ (mL min$^{-1}$ 100 cc$^{-1}$ of tissue), and the fractional plasma volume, fPV (mL cc$^{-1}$ of tissue) by use of suitable models, such as, but not limited to, the two compartment bi-directional model, generally used with macromolecular agents (AJR: 171(4):941–9) or its suitable modifications in which, for example, the contribution due to the agent excretion is considered.

Values of fPV, $K^{PS}$ and $k_2$, wherein $k_2$ in a two compartment bi-directional model is the rate constant denoting the fractional rate of reflux of contrast medium from interstitial water back to plasma, are determined for each contrast agent, and for each tumor, by fitting the dynamic ΔR1(t) data, as an estimator of the contrast agent concentration, C(t), to the appropriate differential equation derived from the following simple relations:

$$C_t = \alpha C_p + (1-\alpha)C_i \quad [1]$$

$$dC_i(t)/dt = K^{PS}.C_p - k_2.C_i \quad [2]$$

$$C_p = A_1.\exp(-b_1.t) + A_2.\exp(-b_2.t) \quad [3]$$

where $C_t$=tissue concentration, $C_p$=plasma (vascular) concentration and $C_i$=interstitial concentration of tracer and α represents the vascular fraction (eq.1). Rate of change of interstitial concentration depends on influx of the contrast agent from plasma and efflux from interstitium (eq.2). $C_p$ (plasma concentration) is given by a biexponential function reflecting body clearance (eq.3). Scalar correction for hematocrit, fractional volumes and time units will be performed where and as appropriate. This model is well-established for the monitoring of dynamic tracer-kinetic data. Suitable software/package will be used for curve plotting and non-linear least squares fitting.

Statistics:

Mean values for $K^{PS}$ and fPV for each contrast agent are compared using unpaired t tests. Pearson correlation analyses are performed comparing the derived values for $K^{PS}$ and fPV with different contrast media in the same tumors. A p value <0.05 will considered statistically significant.

The correlation between the values of fPV and microvascular permeability $K^{PS}$ on the one side and the histological characterisation of the tumor by means of the Scarff-Bloom-Rychardson grading system on the other side is obtained using a linear regression analysis.

Experimental Model for the Urinary and Faecal Excretion Screening of an Intravenously Administered Contrast Agent The experimentation is performed on 6 rats. The animals are intravenously injected (in the marginal caudal vein) with single doses of 0.1 and 1.0 mmol·kg$^{-1}$ of B22956/1 contrast agent at an injection rate of 6 mL/min.

The rats are individually housed in metabolic cages and urine and faeces are collected daily, for 7 days after administration. In particular faeces and urine are collected at the following time periods: 0 to 24 h,and every 24 hours up to 7 days.

The animals are killed by decapitation at 7 days post-dosing and animals blood is collected in heparinised test tubes and then centrifuged for 15 min at 3500·g to separate the plasma. After bleeding, liver, spleen, femurs and kidneys are collected and weighted to evaluate residual content of Gd in the organs. Residual gadolinium concentration in the organic samples is determined by inductively-coupled plasma atomic emission spectrometry (ICP-AES) with a Jobin-Yvon Mod 24 spectrometer Excretion Screening of Rats Injected with B22956/1.

The screening is performed using the contrast compound as 0.25M solution. The agent in intravenously injected in 6 rats with single doses of 0.1 and 1.0 mmol·kg$^{-1}$ of animal body weight.

After intravenous administration of 0.1 mmol·kg$^{-1}$ of B22956/1 Gd was eliminated mainly with faeces and in lesser extent with urine. Particularly, the average cumulative amounts of gadolinium recovered in faeces and in the urine correspond to 88.2±7.9% of the injected dose (ID) and to 9.0±3.7% of the ID respectively. About the 87% of the injected dose is recovered in the faeces within 24 h after injection.

Cumulative urinary and faecal elimination within 7 days after the administration of 0.1 mmol·kg$^{-1}$ dose was from 94 to 102% of the ID.

At the comparative tenfold dose of 1.0 mmol·kg$^{-1}$, Gd was eliminated to the same extent with urine and faeces. On average, gadolinium was recovered in faeces and urine in cumulative amounts corresponding respectively to 39.7±1.4% and to 52.7% of the ID, respectively in the interval between 0 to 7 days after the administration. About the 48% of the injected dose is recovered in the urine, and about 37% of ID in the faeces within 24 h after injection.

Cumulative urinary and faecal elimination within 7 days after the administration of 1.0 mmol·kg$^{-1}$ dose was from 89 to 92% of the ID.

At 7 days after the administration of either 0.1 mmol·kg$^{-1}$ or 1.0 mmol·kg$^{-1}$ of B22956/1, the residual Gd in plasma, liver, spleen, femurs and kidneys was very low or negligible. In particular, the residual content of Gd in plasma was for both the administered doses below the detection limit of 0.05 μg gadolinium/mL by ICP-AES.

Considering a plasma volume in the rat of 40 mL/Kg, the residual Gd in the plasma at 7 days after the administration is, in any case, less than 0.04% of the injected dose.

The invention claimed is:

1. A diagnostic method of assessing microvascular permeability in a tissue or body region using Magnetic Resonance Imaging, said method comprising
   (a) administering to a subject in need of visualization a contrast agent including in its structure chelating unit selected from
   [3β(S),5β]-3-[[4-[bis[2-[bis(carboxymethyl)amino]ethyl]amino]-4-carboxy-1-oxobutyl](carboxymethyl)amino]cholan-24-oic acid;
   [3β(S),5β]-3-[[4-[bis[2-[bis(carboxymethyl)amino]ethyl]amino]-4-carboxy-1-oxobutyl]amino]cholan-24-oic acid;
   [3β(S),5β]-3-[[4-[bis[2-[bis(carboxymethyl)amino]ethyl]amino]-4-carboxy-1-oxobutyl]amino]-12-oxocholan-24-oic acid;
   [3β(S),5β,7α]-3-[[4-[bis[2-[bis(carboxymethyl)amino]ethyl]amino]-4-carboxy-1-oxobutyl]amino]-7-hydroxycholan-24-oic acid;
   2-[[[3β(S),5β]-3-[[4-[bis[2-[bis(carboxymethyl)amino]ethyl]amino]-4-carboxy-1-oxobutyl]amino]-24-oxocholan-24-il]-amino]ethanesulfonic acid;
   [3β(S),5β,12α]-3-[[4-[bis[2-[bis(carboxymethyl)amino]ethyl]amino]-4-carboxy-1-oxobutyl]amino]-12-hydroxycholan-24-oic acid;

[3α(S),5β]-3-[2-[[5-[bis[2-[bis(carboxymethyl)amino]ethyl]amino]-5-carboxypentyl]amino]-2-oxoethoxy]cholan-24-oic acid;

[3β(S),5β,7α,12α]-3-[[4-[bis[2-[bis(carboxymethyl)amino]ethyl]amino]-4-carboxy-1-oxobutyl]amino]-7,12-dihydroxycholan-24-oic acid;

[3β(S),5β,7α,12α]-3-[[4-[[5-bis[2-[bis(carboxymethyl)amino]ethyl]-amino]-5-carboxypentyl]amino]-1,4-dioxobutyl]amino]-7,12-dihydroxycholan-24-oic acid;

(3β,5β,7α,12α)-3-[[[bis[2-[bis(carboxymethyl)amino]ethyl]amino]-acetyl]amino]-7,12-dihydroxycholan-24-oic acid;

(3β,5β)-3-[[[[[bis[2-[bis(carboxymethyl)amino]ethyl]amino]-acetyl]amino]acetyl]amino]-cholan-24-oic acid;

(3β,5β,7α,12α)-3-[[[[[bis[2-[bis(carboxymethyl)amino]ethyl]amino]-acetyl]amino]-acetyl]amino]-7,12-dihydroxycholan-24-oic acid;

(3β,5β,7α,12α)-3-[[6-[[[bis[2-[bis(carboxymethyl)amino]ethyl]amino]-acetyl]amino]-1-oxohexyl]amino]-7,12-dihydroxycholan-24-oic acid;

(3β,5β,7α,12α))-3-[[N-[N-[2-[[2[-bis(carboxymethyl)amino]ethyl]-(carboxymethyl)amino]ethyl]-N-(carboxymethyl)glycyl]glycyl]amino]-7,12-dihydroxycholan-24-oic acid;

18-[[(3β,5β,7α,12α)-23-carboxy-7,12-hydroxy-24-norcholan-3-yl]amino]-3,6,9-tris(carboxymethyl)-11,18-dioxo-3,6,9,12-tetraazaottadecanoic acid;

10-[3-[[(3α,5β,7α,12α))-23-carboxy-7,12-hydroxy-24-norcholan-3-yl]oxy]-2-hydroxypropyl]-1,4,7,10-tetraazacyclododecane-1,4,7-triacetic acid;

[3β(S),5β,7α,12α]-3-[[4-[[5-[[2-[bis(carboxymethyl)amino]ethyl]-(carboxymethyl)amino]-5-carboxypentyl]amino]-1,4-dioxobutyl]amino]-7,12-dihydroxycholan-24-oic acid;

[3β(S),5β]-3-[2-[[5-[[2-[bis(carboxymethyl)amino]ethyl]-(carboxymethyl)amino]-5-carboxypentyl]amino]-2-oxoethoxy]cholan-24-oic acid;

[3β(S),5β,12α]-3-[[4-[[2-[[bis(carboxymethyl)amino]ethyl]-(carboxymethyl)amino]-4-carboxy-1-oxobutyl]amino]-12-hydroxycholan-24-oic acid;

[3β(S),5β]-3-[[4-[[2-[[bis(carboxymethyl)amino]ethyl]-(carboxymethyl)amino]-4-carboxy-1-oxobutyl]amino]-12-oxocholan-24-oic acid;

[3β(S),5β,7α,12α]-3-[[4-[bis[2-[bis(carboxymethyl)amino]ethyl]-amino]-4-carboxy-1-oxobutyl]amino]-7,12-dihydroxycholan-24-oic acid;

[3β(S),5β,7α,12α]-3-[[4-[[5-[bis[2-[bis(carboxymethyl)amino]ethyl]-amino]-5-carboxypentyl]amino]-1,4-dioxobutyl]amino]-7,12-dihydroxycholan-24-oic acid;

[3β(S),5β]-3-[[4-[bis[2-[bis(carboxymethyl)amino]ethyl]amino]-4-carboxy-1-oxobutyl](carboxymethyl)amino]cholan-24-oic acid;

[3β(S),5β]-3-[[4-[bis[2-[bis(carboxymethyl)amino]ethyl]amino]-4-carboxy-1-oxobutyl]amino]cholan-24-oic acid;

[3β(S),5β]-3-[[4-[bis[2-[bis(carboxymethyl)amino]ethyl]amino]-4-carboxy-1-oxobutyl]amino]-12-ossocholan-24-oic acid;

[3β(S),5β,7α]-3-[[4-[bis 2-[bis(carboxymethyl)amino]ethyl]amino]-4-carboxy-1-oxobutyl]amino]-7-hydroxycholan-24-oic acid;

[[[3β(S),5β]-3-[[4-[bis[2-[bis(carboxymethyl)amino]ethyl]amino]-4-carboxy-1-oxobutyl]amino]-24-oxocholan-24-yl]amino]ethanesulfonic acid;

[3β(S),5β,7α]-3-[[4-[bis[2-[bis(carboxymethyl)amino]ethyl]amino]-4-carboxy-1-oxobutyl]amino]-12-hydroxycholan-24-oic acid;

[3α(S),5β]-3-[2-[[5-[bis[2-[bis(carboxymethyl)amino]ethyl]amino]-5-carboxypentyl]amino]-2-oxoethoxy]cholan-24-oic acid;

[3α[3(S),4(S)],5β,12α]-3-[[[trans-3,4-bis[[[5-[bis[2-[bis(carboxymethyl)amino]ethyl]amino]-5-carboxypentyl]amino]carbonyl]-1-pyrrolidinyl]carbonyl]oxy]-12-hydroxycholan-24-oic acid;

[3α[3(S),4(S)],5β,12α]-3-[[[trans-3,4-bis[[[2-[bis[2-[bis(carboxymethyl)amino]ethyl]amino]-2-carboxyethyl]amino]carbonyl]-1-pyrrolidinyl]carbonyl]oxy]-12-hydroxycholan-24-oic acid;

(3α,5β,12α)-3-[[[trans-3,4-bis[[[2-[[4,7,10-tris(carboxymethyl)-1,4,7,10-tetraazacyclododec-1-yl]acetyl]amino]ethyl]amino]carbonyl]-1-pyrrolidinyl]carbonyl]oxy]-12-hydroxycholan-24-oic acid

[3α[3(S),4(S)],5β,12α]-3-[[[trans-3,4-bis[[[5-[[2-[bis(carboxymethyl)amino]ethyl](carboxymethyl)amino]-5-carboxypentyl]amino]-carbonyl]-1-pyrrolidinyl]carbonyl]oxy]-12-hydroxycholan-24-oic acid;

[3α[1(S),2(S)],5β,7α,12α]-3-[[[[cis-1,2-bis[[[5-[bis[2-[bis(carboxymethyl)amino]ethyl]amino]-5-carboxypentyl]amino]carbonyl]-4-cyclopentyl]amino]carbonyl]oxy]-7,12-dihydroxycholan-24-oic acid;

[3α[1(S)],5β,7α,12α]-3-[[[[cis-1-[[[5-[bis[2-[bis(carboxymethyl)-amino]ethyl]amino]-5-carboxypentyl]amino]carbonyl]-2-[[[2-[[[4,7,10-tris(carboxymethyl)-1,4,7,10-tetraazacyclododec-1-yl]acetyl]amino]ethyl]amino]carbonyl]-4-cyclopentyl]amino]carbonyl]oxy]-7,12-dihydroxycholan-24-oic acid; and

[3β[3(S),5(S)],5β,7α,12α]-3-[[[3,5-bis[[4-[bis[2-[bis(carboxymethyl)-amino]ethyl]amino]-4-carboxy-1-oxobutyl]amino]phenyl]carbonyl]amino]-7,12-dihydroxycholan-24-oic acid and a paramagnetic bi- or trivalent metal ion selected from the group consisting of gadolinium (III), iron (III), iron (II), manganese (II), manganese (III), chromium (III), copper (II), dysprosium (III), ytterbium (III), terbium (III) and europium (III), and a physiologically compatible organic base selected from primary, secondary, or tertiary amines or basic amino acid, or with an inorganic base who cations are selected from sodium, potassium, magnesium calcium or mixtures thereof, (b) monitoring the enhancement in said tissue or body region by use of MRI, and (c) determining the microvascular permeability in said tissue or body region based on rate of the enhancement increase.

2. The method according to claim 1 for the diagnostic assessment of the microvessels integrity.

3. The method according to claim 1 for the determination of the microvascular permeability.

4. The method according to claim 1 for the determination of a fractional plasma volume of a human or animal body tissue.

5. The method according to claim 1 wherein the assessment of a human or animal body tissue pathologic condition is performed based on a quantitative evaluation of microvascular permeability and fractional plasma volume characteristics, wherein the pathological condition is selected from tumors of the oral cavity, bladder, brain, mammary, cervix, ovaries, pancreas, lung, prostate, soft tissue, central nervous system tumors, and carcinomas.

6. The method according to claim 5 for the diagnostic assessment of the angiogenesis.

7. The method according to claim 5 to determine the histopathologic grade of a tumor mass.

8. The method according to claim 1 wherein the assessment of a human or animal body tissue pathologic condition is performed based on a quantitative evaluation of microvascular permeability and fractional plasma volume characteristics, wherein the pathological condition is selected from inflammation, myocardial and ischemic states.

9. The method according to claim 8 wherein the method provides diagnostic assessment of inflammatory states.

10. The method according to claim 8 to perform a diagnostic assessment of myocardial or cerebral ischemic states.

11. The method according to claim 6 to monitor the malignancy response to an angiogenesis inhibitor.

12. The method according to claim 11 wherein the angiogenesis inhibition is performed with a human anti-VEGF monoclonal antibody.

13. The method according to claim 6 to monitor the malignancy response to chemotherapy or radiation therapy.

14. The method according to claim 5 to define embryogenesis, wound healing, corpus luteum formation and growth.

15. The method according to claim 1 wherein the diagnostic imaging is performed by Contrast Enhanced Dynamic Magnetic Resonance Imaging (DCE MRI).

16. The method according to claims 1 or 15 wherein the agent is the gadolinium complex of the [3β(S),5β,12α]-3-[[4-[bis[2-[bis(carboxymethyl)amino]ethyl]amino]-4-carboxy-1-oxobutyl]amino]-12-hydroxycholan-24-oic acid.

17. The method according to claim 16 wherein said agent is in the form of a trisodium salt.

* * * * *